(12) United States Patent
Fourtillan et al.

(10) Patent No.: US 7,291,627 B2
(45) Date of Patent: Nov. 6, 2007

(54) DIHYDROIMIDAZO[5.1-A]-BETA-CARBOLINE DERIVATIVES, METHOD FOR THEIR PREPARATION, AND THEIR APPLICATION AS A DRUG

(75) Inventors: Jean-Bernard Fourtillan, Bordeaux (FR); Marianne Fourtillan, Bordeaux (FR); Omar Karam, Saint-Benoit (FR); Fabien Zunino, Buxerolles (FR); Jean-Claude Jacquesy, Buxerolles (FR); Jean-Pierre Tafani, Maisons Alfort (FR)

(73) Assignee: MACEF, Migne-Auxances (FR)

( * ) Notice: Subject to any disclaimer, the term of this patent is extended or adjusted under 35 U.S.C. 154(b) by 283 days.

(21) Appl. No.: 10/478,002

(22) PCT Filed: May 16, 2002

(86) PCT No.: PCT/FR02/01653

§ 371 (c)(1), (2), (4) Date: Dec. 3, 2004

(87) PCT Pub. No.: WO02/092598

PCT Pub. Date: Nov. 21, 2002

(65) Prior Publication Data

US 2006/0089372 A1   Apr. 27, 2006

(30) Foreign Application Priority Data

May 16, 2001   (FR) .................................. 01 06444

(51) Int. Cl.
*A61K 31/437* (2006.01)
*C07D 471/12* (2006.01)

(52) U.S. Cl. ........................................ 514/287; 546/64
(58) Field of Classification Search ............... 514/287; 546/64

See application file for complete search history.

(56) References Cited

U.S. PATENT DOCUMENTS 6,048,868 A   4/2000   Fourtillan et al.

FOREIGN PATENT DOCUMENTS

| WO | WO 95/24191   | 9/1995 |
| WO | WO 95/24191 A | 9/1995 |
| WO | WO 96/08490   | 3/1996 |
| WO | WO 96/08490 A | 3/1996 |
| WO | WO 99/47521   | 9/1999 |
| WO | WO 99/47521 A | 9/1999 |

OTHER PUBLICATIONS

Goodman & Gilman's The Pharmacological Basis of Therapeutics, 10th edition, McGraw-Hill, New York, New York, 2001, Chapter 17, pp. 399-427.

ADA Sedative Hypnotics, http://www.well.com/user/woa/fsseda.htm, Jun. 9, 2006.

Hypnotic, http://en.wikipedia.org/wiki/Hypnotic, Jun. 9, 2006.

MeReC Bulletin, vol. 15, No. 5, Apr. 2005, published by the NHS, pp. 17-20.

Trujillo et al, Drugs and the Brain, California State University, "Sedative-Hypnotics," http://www/csusm.edu/DandB/Sedatives.html, Jun. 6, 2006.

Medline Plus, Medical Encyclopedia: Hypnotics, http://www.nlm.nih.gov/medlineplus/print/ency/article/002376.htm, Jun. 9, 2006.

Sedative-Hypnotics, Dec. 23, 2000, http://www.toad.net/~arcturus/dd/sedative.htm, Jun. 9, 2006.

Crankshaw, Hypnotics in infusion anaesthesia, "Anaesth Intensive Care," Feb. 1987, 15(1) 90-66, abstract at http://www.general-anaesthesia.com/hypnotics.html, Jun. 9, 2006.

Hypnotics, http://www.humed.com/humc_ency/ency/article/002376.htm, Jun. 9, 2006.

Database Chemical Abstracts Service, Abstract XP-002185124; Kanaoka, Yuichi et al., "Amino acids and Peptides. II. Cyclodehydration of some tryptophan-dipeptides and their derivatives with a . . . "

J. Elliott, *J. Org. Chem.*, (1962), vol. 27, pp. 3302-3305, "Synthesis of Imidazo[5,1-α]isoquinoline and β-Carboline Derivatives."

Kanaoka, Yuichi et al., "*Amino Acids and Peptides. II. Cyclodehydration of Some Tryptophan-Dipeptides and Their Derivatives with a Polyphosphate Ester*," Chemical Abstracts Service, Columbus, Ohio, Database Accession No. 68:78590 XP002185124 & Tetrahedron (1968), 24(6), 2591-4.

(Continued)

*Primary Examiner*—Charanjit S. Aulakh
(74) *Attorney, Agent, or Firm*—Buchanan, Ingersoll & Rooney, PC

(57) ABSTRACT

The invention concerns dihydroimidazo[5,1-a]-β-carboline compounds of general formula (I)

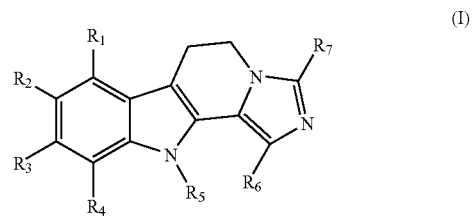

wherein in particular, $R_1$, $R_2$, $R_3$, $R_4$, $R_6$ and $R_7$, identical or different, independently of one another, present a hydrogen, halogen atom, an alkyl, hydroxyl, alkoxy, trihalogenoalkyl, alkylamino, dialkylamino, aryl, arylalkyl, carboxy, alkylcarbonyloxy, acyl, aryloxy or arylalkoxy group; $R_5$ represents a hydrogen atom, an alkyl or arylalkyl group; and their isomers as well as their addition salts to a pharmaceutically acceptable acid. The inventive compounds are for use in medicine, in particular as hypnotics.

14 Claims, No Drawings

DIHYDROIMIDAZO[5.1-A]-BETA-CARBOLINE DERIVATIVES, METHOD FOR THEIR PREPARATION, AND THEIR APPLICATION AS A DRUG

The present invention concerns novel derivatives of dihydroimidazo[5,1-a]-β-carboline with general formula (I):

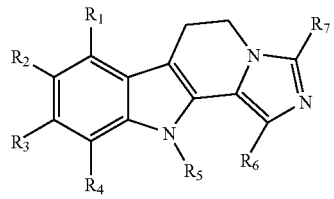

in which:

$R_1$, $R_2$, $R_3$ and $R_4$, which may be identical or different, independently represent a hydrogen atom, a halogen atom, a linear or branched ($C_1$-$C_6$) alkyl group, a hydroxyl group, a linear or branched ($C_1$-$C_6$) alkoxy group, a linear or branched trihalogeno ($C_1$-$C_6$)alkyl group, a linear or branched trihalogeno ($C_1$-$C_6$)alkoxy group, a nitro group, a cyano group, an amino group, a linear or branched ($C_1$-$C_6$) alkylamino group, a linear or branched di($C_1$-$C_6$)alkylamino group, an aryl group, a linear or branched aryl($C_1$-$C_6$)alkyl group, a carboxyl group, a linear or branched ($C_1$-$C_6$) alkylcarbonyloxy group, a linear or branched ($C_1$-$C_6$) acyl group, an aryloxy group or a linear or branched aryl($C_1$-$C_6$) alkoxy group;

$R_5$ represents a hydrogen atom, a linear or branched ($C_1$-$C_6$) alkyl group or a linear or branched aryl($C_1$-$C_6$)alkyl group;

$R_6$ and $R_7$, which may be identical or different, independently represent a hydrogen atom, a halogen atom, a linear or branched ($C_1$-$C_6$) alkyl group, a hydroxyl group, a linear or branched ($C_1$-$C_6$) alkoxy group, a linear or branched trihalogeno($C_1$-$C_6$)alkyl group, a linear or branched trihalogeno($C_1$-$C_6$)alkoxy group, a cyano group, an amino group, a linear or branched ($C_1$-$C_6$)alkylamino group, a linear or branched di($C_1$-$C_6$)alkylamino group, an aryl group, a linear or branched aryl($C_1$-$C_6$)alkyl group, a carboxyl group, a linear or branched ($C_1$-$C_6$)alkylcarbonyloxy group, a linear or branched ($C_1$-$C_6$) acyl group, an aryloxy group or a linear or branched aryl($C_1$-$C_6$)alkoxy group; their isomers and their addition salts with a pharmaceutically acceptable acid.

In the present description, the term "aryl" means a phenyl, naphthyl, tetrahydronaphthyl, dihydronaphthyl, indenyl or indanyl group, each of said groups optionally being substituted, in an identical or different manner, with one or more halogen atoms, hydroxyl, cyano, nitro, linear or branched ($C_1$-$C_6$) alkyl, linear or branched ($C_1$-$C_6$) alkoxy, amino, linear or branched ($C_1$-$C_6$) alkylamino, linear or branched di ($C_1$-$C_6$)alkylamino, aryloxy, linear or branched aryl($C_1$-$C_6$) alkoxy, linear or branched ($C_1$-$C_6$)trihalogenoalkyl, linear or branched ($C_1$-$C_6$) acyl, linear or branched ($C_1$-$C_6$)alkoxycarbonyl, linear or branched ($C_1$-$C_6$) alkylaminocarbonyl or oxo groups.

In an advantageous variation, preferred compounds of the invention are those in which:

$R_1$, $R_3$ and $R_4$ represent a hydrogen atom;

$R_6$ and $R_7$ independently represent a hydrogen atom, a linear or branched ($C_1$-$C_6$) alkyl group or an aryl group; and $R_5$ represents a hydrogen atom, or a linear or branched ($C_1$-$C_6$) alkyl group.

Preferred substituents $R_2$ in accordance with the invention are a hydrogen atom, a halogen atom (fluorine, chlorine or bromine), a linear or branched ($C_1$-$C_6$) alkyl group, a hydroxyl group and a linear or branched ($C_1$-$C_6$) alkoxy group.

Preferred compounds of the invention are:

3,11-dimethyl-5,6-dihydroimidazo[5,1-a]-β-carboline methane sulfonate;

8-methoxy-3-methyl-5,6-dihydroimidazo[5,1-a]-β-carboline methane sulfonate;

8-methoxy-5,6-dihydroimidazo[5,1-a]-β-carboline;

8-methoxy-3-methyl-1-phenyl-5,6-dihydroimidazo[5,1-a]-β-carboline;

1-ethyl-8-methoxy-3-methyl-5,6-dihydroimidazo[5,1-a]-β-carboline;

8-methoxy-3-isopropyl-5,6-dihydroimidazo[5,1-a]-β-carboline;

8-methoxy-3-propyl-5,6-dihydroimidazo[5,1-a]-β-carboline;

8-methoxy-11-methyl-3-propyl-5,6-dihydroimidazo[5,1-a]-β-carboline methane sulfonate;

8-methoxy-3,11-dimethyl-5,6-dihydroimidazo[5,1-a]-β-carboline methane sulfonate;

8-hydroxy-3,11-dimethyl-5,6-dihydroimidazo[5,1-a]-β-carboline methane sulfonate;

8-hydroxy-3-methyl-5,6-dihydroimidazo[5,1-a]-β-carboline methane sulfonate;

3-methyl-5,6-dihydroimidazo[5,1-a]-β-carboline methane sulfonate;

8-chloro-3-methyl-5,6-dihydroimidazo[5,1-a]-β-carboline methane sulfonate;

8-methoxy-3-phenyl-5,6-dihydroimidazo[5,1-a]-β-carboline;

11-ethyl-3-methyl-5,6-dihydroimidazo[5,1-a]-β-carboline methane sulfonate;

8-chloro-3,11-dimethyl-5,6-dihydroimidazo[5,1-a]-β-carboline methane sulfonate;

8-chloro-3-methyl-11-ethyl-5,6-dihydroimidazo[5,1-a]-β-carboline methane sulfonate;

3,8-dimethyl-5,6-dihydroimidazo[5,1-a]-β-carboline methane sulfonate;

3,8,11-trimethyl-5,6-dihydroimidazo[5,1-a]-β-carboline methane sulfonate;

11-ethyl-3,8-dimethyl-5,6-dihydroimidazo[5,1-a]-β-carboline methane sulfonate;

8-fluoro-3-methyl-5,6-dihydroimidazo[5,1-a]-β-carboline methane sulfonate;

8-bromo-3-methyl-5,6-dihydroimidazo[5,1-a]-β-carboline methane sulfonate;

8-fluoro-3,11-dimethyl-5,6-dihydroimidazo[5,1-a]-β-carboline methane sulfonate;

8-fluoro-11-ethyl-3-methyl-5,6-dihydroimidazo[5,1-a]-β-carboline methane sulfonate;

8-bromo-11-ethyl-3-methyl-5,6-dihydroimidazo[5,1-a]-β-carboline methane sulfonate.

The invention also pertains to a method for preparing compounds with formula (I), characterized in that the starting product used is a compound with formula (II):

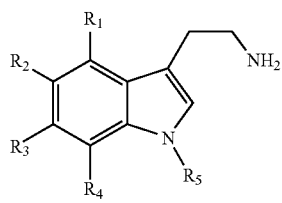

in which $R_1$, $R_2$, $R_3$, $R_4$ and $R_5$ have the meanings given in formula (I), said compound with formula (II) being reacted under peptide coupling synthesis conditions with a compound with formula (III):

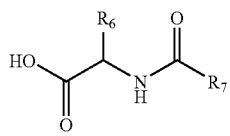

in which $R_6$ and $R_7$ are as defined in formula (I), to produce a compound with formula (IV):

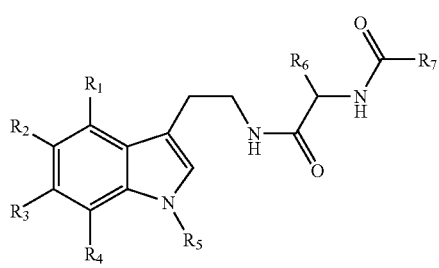

in which $R_1$, $R_2$, $R_3$, $R_4$, $R_5$, $R_6$ and $R_7$ are as defined above, the compound with formula (IV) being treated in the presence of phosphorous oxychloride in a solvent such as toluene to produce compounds with formula (I):

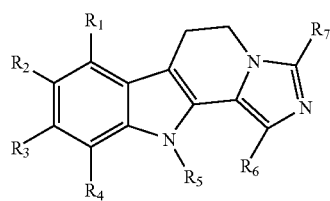

in which $R_1$, $R_2$, $R_3$, $R_4$, $R_5$, $R_6$ and $R_7$ are as defined above, the compounds with general formula (I) together forming the compounds of the invention which are transformed if appropriate into their addition salts with a pharmaceutically acceptable acid.

The compounds with formula (II) and (III) are either commercially available compounds, or are obtained using known methods of organic synthesis.

The present invention also pertains to pharmaceutical compositions comprising, as the active principle, at least one compound with formula (I), its addition salts with a pharmaceutically acceptable acid, used alone or in combination with one or more nontoxic and pharmaceutically acceptable excipients or inert vehicles.

More particular pharmaceutical compositions of the invention that can be cited are those which are suitable for oral, parenteral (intravenous, intramuscular or subcutaneous), per- or transcutaneous, nasal, rectal, perlingual, ocular or respiratory administration, and in particular as simple or sugar-coated tablets, sublingual tablets, sachets, gelules, lozenges, suppositories, creams, pomades, skin gels, injectable or drinkable preparations, aerosols, or eye or nose drops.

The following examples illustrate the invention without in any way limiting its scope.

Dihydroimidazo[5,1-a]-β-carboline derivatives have been described in the prior art as intermediates in the synthesis of the following:

$R_1=R_2=R_3=R_4=R_5=R_6=H$ and $R_7=CH_3$: Kanaoke Y; Sato E; Yonemitsu O; *Tetrahedron*, 1968, 24, 2591-2594.

$R_1=R_2=R_3=R_4=R_5=R_6=H$ and $R_7=Ph$: Elliott, *J. Org. Chem.*, 1962, 3302-3305.

Clearly, those derivatives are only described as intermediates in a synthesis and have no known therapeutic activity. They only fall within the scope of the present invention in the context of a drug, in particular as a hypnotic.

The starting products and/or the reagents used are products that are known or prepared using known methods.

The structures of the compounds described in the examples and the stages of the synthesis were determined using the usual spectrophotometric techniques (infrared, NMR, mass spectroscopy).

In order to illustrate the subject matter of the present invention, there follow some examples of derivatives with general formula I in which $R_1=R_3=R_4=H$:

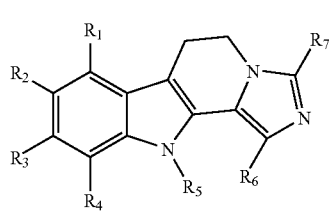

TABLE I

| EXAMPLE | $R_2$ | $R_5$ | $R_6$ | $R_7$ |
|---|---|---|---|---|
| Example 1 | H | $CH_3$ | H | $CH_3$ |
| Example 2 | $CH_3O$ | H | H | $CH_3$ |
| Example 3 | $CH_3O$ | H | H | H |
| Example 4 | $CH_3O$ | H | Ph | $CH_3$ |
| Example 5 | $CH_3O$ | H | $CH_3CH_2$ | $CH_3$ |
| Example 6 | $CH_3O$ | H | H | $CH(CH_3)_2$ |
| Example 7 | $CH_3O$ | H | H | $(CH_2)_2CH_3$ |
| Example 8 | $CH_3O$ | $CH_3$ | H | $(CH_2)_2CH_3$ |
| Example 9 | $CH_3O$ | $CH_3$ | H | $CH_3$ |
| Example 10 | OH | $CH_3$ | H | $CH_3$ |
| Example 11 | OH | H | H | $CH_3$ |
| Example 12 | H | H | H | $CH_3$ |
| Example 13 | Cl | H | H | $CH_3$ |
| Example 14 | $CH_3O$ | H | H | Ph |
| Example 15 | H | $CH_3CH_2$ | H | $CH_3$ |
| Example 16 | Cl | $CH_3$ | H | $CH_3$ |
| Example 17 | Cl | $CH_3CH_2$ | H | $CH_3$ |
| Example 18 | $CH_3$ | H | H | $CH_3$ |

TABLE I-continued

| EXAMPLE | $R_2$ | $R_5$ | $R_6$ | $R_7$ |
|---|---|---|---|---|
| Example 19 | $CH_3$ | $CH_3$ | H | $CH_3$ |
| Example 20 | $CH_3$ | $CH_3CH_2$ | H | $CH_3$ |
| Example 21 | F | H | H | $CH_3$ |
| Example 22 | Br | H | H | $CH_3$ |
| Example 23 | F | $CH_3$ | H | $CH_3$ |
| Example 24 | F | $CH_3CH_2$ | H | $CH_3$ |
| Example 25 | Br | $CH_3CH_2$ | H | $CH_3$ |

EXAMPLE 1

3,11-dimethyl-5,6-dihydroimidazo[5,1-a]-β-carboline methane sulfonate

Operating Mode A 2-acetylamino-N-[2-(1H-indol-3-yl)-ethyl]acetamide

Diphenylphosphorylazide (5.8 ml, 27.5 ml) and triethylamine (3.85 ml, 27.5 ml) were added in succession to a mixture of tryptamine (4.32 g, 27 mmol) and N-acetylglycine (3.3 g, 28 mmol) in DMF (100 ml) cooled to 0° C. The mixture was stirred under nitrogen at ambient temperature for 12 h, then the solvent was eliminated under reduced pressure. The residue obtained was flash chromatographed on silica gel to produce the expected product (m=5.5 g, 21 mmol), giving a yield of 78%.

Operating Mode B 2-acetylamino-N-[2-(1-methyl-1H-indol-3-yl)-ethyl] acetamide

NaH at 60% in oil (0.35 g, 8.75 mmol) and an alkyl halide ($CH_3I$, 0.55 ml, 8.83 mmol) were added to the amide (2 g, 8.23 mmol) obtained in operating mode A in DMF (20 ml). It was stirred for 12 hours at ambient temperature before eliminating the solvent under reduced pressure. The expected product was obtained after flash chromatography on silica gel (1.02 g, 3.96 mmol), giving a yield of 48%.

Operating Mode C 3,11-dimethyl-5,6-dihydroimidazo-[5,1-a]-β-carboline methane sulfonate The amide (1.02 g, 3.96 mmol) from operating mode B was heated to reflux in toluene (V=50 ml). $POCl_3$ (10 ml) in toluene (15 ml) was added over 30 min. The reaction mixture was concentrated under reduced pressure and the residue was taken up in ethanol (5 ml), then NaOH was added (20%, 50 ml). It was stirred for 30 min, then the solid formed was recovered by filtering. The product was purified by flash chromatography on silica gel; the expected product was obtained (280 mg, 1.26 mmol; Yield=32%).

To obtain 3,11-dimethyl-5,6-dihydroimidazo[5,1-a]-β-carboline methane sulfonate dissolved in ethanol, methane sulfonic acid (1 equivalent) was added and the corresponding mesylate was obtained by precipitation.

$^1$H NMR (300 MHz, $CDCl_3$): 2.72 (s, 3H); 2.78 (s, 3H); 3.23 (t, J=6.9 Hz, 2H), 3.71 (s, 3H); 4.22 (t, J =6.9 Hz, 2H); 7.11 (m, 2H); 7.24 (s, 2H); 7.48 (m, 2H).
MS (m/z) 237 (100); 221; 195; 181.

EXAMPLE 2

8-methoxy-3-methyl-5,6-dihydroimidazo[5,1-a]-β-carboline methane sulfonate

The procedure of Example 1 was followed using 5-methoxytryptamine and N-acetylglycine as substrate during operating mode A; the amide obtained was used directly in the cyclization reaction of operating mode C.
$^1$H NMR (300 MHz, $CDCl_3$): 2.40 (s, 3H); 2.80 (s, 3H); 3.00 (t, J=6.6 Hz, 2H), 3.80 (s, 3H); 3.96 (t, J=6.6 Hz, 2H); 6.78 (m, 2H); 7.20 (d, J=8.8 Hz, 1H), 7.50 (s, 1H).

EXAMPLE 3

8-methoxy-5,6-dihydroimidazo[5,1-a]-β-carboline

The procedure of Example 1 was followed using 5-methoxytryptamine and N-formylglycine as substrate during operating mode A; the amide obtained was used directly in the cyclization reaction of operating mode C.
$^1$H NMR (300 MHz, $CDCl_3$:$CD_3OD$/90:10): 3.09 (t, J=6.9 Hz, 2H); 3.82 (s, 3H); 4.2 (t, J=6.9 Hz, 2H); 6.79 (dd, J=2.4 and 8.8 Hz, 1H); 6.91 (d, J=2.4 Hz, 1H); 7.10 (s, 1H); 7.23 (d, J=8.8 Hz, 1H); 7.50 (s, 1H).
MS (m/z) 239 (100); 196; 168; 140.

EXAMPLE 4

8-methoxy-3-methyl-1-phenyl-5,6-dihydro-imidazo [5,1-a]-β-carboline

The procedure of Example 1 was followed using 5-methoxytryptamine and N-acetyl-2-phenylglycine as substrate during operating mode A; the amide obtained was used directly in the cyclization reaction of operating mode C.
$^1$H NMR (300 MHz, $CDCl_3$): 2.5 (s, 2H); 3.15 (t, J=6.9 Hz, 2H); 3.85 (s, 3H), 4.08 (t, J=6.9 Hz, 2H); 6.8 (dd, J=2.4 and 8.8 Hz, 1H); 6.94 (d, J=2.4 Hz, 1H); 7.15 (d, J=8.8 Hz, 1H); 7.36 (m, 1H); 7.46 (m, 2H); 7.74 (m, 2H); 8.30 (s, 1H).
MS (m/z) 329 (100); 286; 165; 143.

EXAMPLE 5

1-ethyl-8-methoxy-3-methyl-5,6-dihydro-imidazo[5,1-a]-β-carboline

The procedure of Example 1 was followed using 5-methoxytryptamine and N-acetyl-2-ethylglycine as substrate during operating mode A; the amide obtained was used directly in the cyclization reaction of operating mode C.
$^1$H NMR (300 MHz, $CDCl_3$): 1.30 (t, 7 Hz, 3H); 2.43 (s, 3H); 2.80 (q, 7 Hz, 2H); 3.11 (t, J=7 Hz, 2H); 3.88 (s, 3H), 4.06 (t, J=7 Hz, 2H); 6.83 (dd, J=2.4 and 8.7 Hz, 1H); 6.97 (d, J=2.4 Hz, 1H); 7.27 (d, J=8.7 Hz, 1H); 8.71 (broad s, 1H).
MS (m/z) 281 (100); 266; 250; 233.

EXAMPLE 6

8-methoxy-3-isopropyl-5,6-dihydroimidazo-[5,1-a]-β-carboline

The procedure of Example 1 was followed using 5-methoxytryptamine and N-isobutyrylglycine as substrate during operating mode A; the amide obtained was used directly in the cyclization reaction of operating mode C.

$^1$H NMR (300 MHz, CDCl$_3$:CD$_3$OD/90:10): 1.33 (d, J=6.8 Hz, 6H); 3.04 (m, 4H); 3.86 (s, 3H); 4.04 (t, J=6.8 Hz, 2H); 6.79 (d, J=8.76 Hz, 1H), 6.95 (s, 1H); 6.98 (s, 1H); 7.22 (d, J=8.76 Hz, 1H); 10.30 (s, 1H).

MS (m/z) 281 (100); 266; 196; 133

EXAMPLE 7

8-methoxy-3-propyl-5,6-dihydroimidazo[5,1-a]-β-carboline

The procedure of Example 1 was followed using 5-methoxytryptamine and N-butyrylglycine as substrate during operating mode A; the amide obtained was used directly in the cyclization reaction of operating mode C.

$^1$H NMR (300 MHz, CDCl$_3$): 1.00 (t, 7.5 Hz, 3H); 1.76 (m, 2H); 2.70 (t, 7.5 Hz, 2H); 3.08 (t, J=7.5 Hz, 2H); 3.87 (s, 3H); 3.97 (t, J=7.5 Hz, 2H); 6.81 (dd, J=2.7 and 8.7 Hz, 1H), 6.88 (d, J=2.7 Hz, 1H); 7.08 (s, 1H); 7.28 (d, J=8.7 Hz, 1H); 10.38 (broad s, 1H).

MS (m/z) 281 M+; 269; 252 (100); 209.

EXAMPLE 8

8-methoxy-11-methyl-3-propyl-5,6-dihydro-imidazo[5,1-a]-β-carboline methane sulfonate The procedure of Example 1 was followed using 5-methoxytryptamine and N-butyrylglycine as substrate during operating mode A.

$^1$H NMR (300 MHz, CDCl$_3$:CD$_3$OD/90:10): 1.06 (t, 7.5 Hz, 3H); 1.83 (m, 2H); 2.75 (t, 7.5 Hz, 2H); 3.08 (t, J=6.8 Hz, 2H); 3.8 (s, 3H); 3.88 (s, 3H); 4.06 (t, J=6.8 Hz, 2H); 6.86 (dd, J=2.4 and 8.7 Hz, 1H), 6.96 (d, J=2.4 Hz, 1H); 7.15 (s, 1H); 7.18 (d, J=8.7 Hz, 1H).

MS (m/z) 295 (100); 266; 223; 133.

EXAMPLE 9

8-methoxy-3,11-dimethyl-5,6-dihydroimidazo-[5,1-a]-β-carboline methane sulfonate The procedure of Example 1 was followed using 5-methoxytryptamine and N-acetylglycine as substrate during operating mode A.

$^1$H NMR (300 MHz, CDCl$_3$:CD$_3$OD/90:10): 2.44 (s, 3H); 3.05 (t, J=6.9 Hz, 2H); 3.77 (s, 3H); 3.85 (s, 3H); 3.99 (t, J=6.9 Hz, 2H); 6.86 (dd, J=2.4 and 8.7 Hz, 1H); 6.93 (d, J=2.4 Hz, 1H); 7.15 (d, J=8.7 Hz, 1H).

MS (m/z) 267 (100); 251; 235; 224.

EXAMPLE 10

8-hydroxy-3,11-dimethyl-5,6-dihydroimidazo-[5,1-a]-β-carboline methane sulfonate 8-methoxy-3,11-dimethyl-5,6-dihydroimidazo[5,1-a]-β-carboline (Example 9, m=300 mg, 1 mmol) was dissolved in anhydrous dichloromethane at −78° C. BBr$_3$ (V=8 ml) was added and the temperature was allowed to return to ambient temperature over 12 hours with stirring and in a nitrogen atmosphere. A solution of (2M) NaHCO$_3$ (15 ml) was added. After decanting, the product precipitated from the dichloromethane and the expected product was recovered (m=150 mg, 0.6 mmol, Yield=50%).

$^1$H NMR (300 MHz, CDCl$_3$:CD$_3$OD/90:10): 2.45 (s, 3H); 3.05 (t, J=6.7 Hz, 2H); 3.84 (s, 3H); 4.06 (t, J=6.7 Hz, 2H); 6.80 (d, J=8.7 Hz, 1H), 6.91 (s, 1H); 7.15 (d, J=8.7 Hz, 1H).

MS (m/z) 253 (100); 224; 211; 126.

EXAMPLE 11

8-hydroxy-3-methyl-5,6-dihydroimidazo[5,1-a]-β-carboline methane sulfonate 8-methoxy-3-methyl-5,6-dihydroimidazo[5,1-a]-β-carboline (Example 2, m=350 mg, 1.4 mmol) was dissolved in anhydrous dichloromethane at −78° C. BBr$_3$ (V=8 ml) was added and the temperature was allowed to return to ambient temperature over 12 hours with stirring and in a nitrogen atmosphere. A solution of (2M) NaHCO$_3$ (15 ml) was added. After decanting, the product precipitated from the dichloromethane and the expected product was recovered (m=200 mg, 0.83 mmol, Yield=59%).

$^1$H NMR (300 MHz, CDCl$_3$:CD$_3$OD/90:10): 2.67 (s, 3H); 3.19 (t, J=7.2 Hz, 2H); 4.21 (t, J=7.2 Hz, 2H); 6.78 (dd, J=2.4 and 8.7 Hz, 1H), 6.88 (d, J=2.4 Hz, 1H); 7.23 (d, J=8.7 Hz, 1H).

EXAMPLE 12

3-methyl-5,6-dihydroimidazo[5,1-a]-β-carboline methane sulfonate

The procedure of Example 1 was followed using tryptamine and N-acetylglycine as substrate during operating mode A. The amide obtained was used directly in the cyclization reaction of operating mode C.

$^1$H NMR (300 MHz, CDCl$_3$): 2.53 (s, 3H); 3.08 (t, J=6.8 Hz, 2H); 3.99 (t, 6.8 Hz, 2H); 7.04 (m, 2H); 7.16 (m, 2H); 7.36 (s, 1H); 7.44 (d, 1H).

MS (m/z) 223 (100); 208; 181; 154.

EXAMPLE 13

8-chloro-3-methyl-5,6-dihydroimidazo[5,1-a]-β-carboline methane sulfonate

The procedure of Example 1 was followed using 5-chlorotryptamine and N-acetylglycine as substrate during operating mode A. The amide obtained was used directly in the cyclization reaction of operating mode C.

$^1$H NMR (300 MHz, CDCl$_3$:CD$_3$OD/90:10): 2.72 (s, 3H); 2.81 (s, 3H); 3.16 (t, J=6.9 Hz, 2H); 4.13 (t, J=6.9 Hz, 2H); 7.12 (dd, J=2 and 8.7 Hz, 1H); 7.31 (d, J=8.7 Hz, 1H); 7.44 (d, J=2 Hz, 1H); 7.52 (s, 1H).

MS (m/z) 257 (100); 242; 221; 215.

EXAMPLE 14

8-methoxy-3-phenyl-5,6-dihydroimidazo[5,1-a])-β-carboline

The procedure of Example 1 was followed using 5-methoxytryptamine and hippuric acid as substrate during operating mode A. The amide obtained was used directly in the cyclization reaction of operating mode C.

$^1$H NMR (300 MHz, CD$_3$COCD$_3$): 2.87 (s, 3H); 3.16 (t, J=6.8 Hz, 2H); 3.82 (s, 3H), 4.45 (t, J=6.8 Hz, 2H); 6.77 (dd,

J=2.4 and 9.6 Hz, 1H); 7.05 (d, J=2.4 Hz, 1H); 7.30 (s, 1H); 7.31 (d, J=9.6 Hz, 1H); 7.52 (m, 3H); 7.75 (m, 2H); 8.02 (s, 1H).

MS (m/z) 315 (100); 272; 211; 168.

EXAMPLE 15

11-ethyl-3-methyl-5,6-dihydroimidazo[5,1-a]-β-carboline methane sulfonate

The procedure of Example 1 was followed using tryptamine and N-acetylglycine as substrate during operating mode A. The alkylation agent for operating mode B was ethyl bromide.

$^1$H NMR (300 MHz, $CD_3OD$): 1.33 (t, 7.1 Hz, 3H); 2.76 (s, 3H); 2.78 (s, 3H); 3.25 (t, J=6.9 Hz, 2H); 4.24 (m, 4H); 7.12 (t, 1H); 7.3 (m, 2H); 7.49 (d+1s, 2H).

EXAMPLE 16

8-chloro-3,11-dimethyl-5,6-dihydroimidazo-[5,1-a]-β-carboline methane sulfonate

The procedure of Example 1 was followed using 5-chlorotryptamine and N-acetylglycine as substrate during operating mode A.

$^1$H NMR (300 MHz, $CDCl_3$): 2.60 (s, 3H); 2.70 (s, 3H); 3.16 (t, J=6.8 Hz, 2H); 4.20 (t, J=6.8 Hz, 2H); 7.12 (d, J=8.8 Hz, 1H); 7.25 (d, J=8.8 Hz, 1H); 7.50 (s, 1H); 7.6 (s, 1H).

MS (m/z): 271 (100); 235; 193; 167.

EXAMPLE 17

8-chloro-3-methyl-11-ethyl-5,6-dihydro-imidazo[5,1-a]-β-carboline methane sulfonate The procedure of Example 1 was followed using 5-chlorotryptamine and N-acetylglycine as substrate during operating mode A. The alkylation agent for operating mode B was ethyl bromide.

$^1$H NMR (300 MHz, $CDCl_3$): 1.39 (t, J=4.8 Hz, 3H); 2.70 (s, 3H); 2.85 (s, 3H); 3.2 (t, J=7 Hz, 2H); 4.3 (m, 4H); 7.2 (dd, J=2.4 and 8.8 Hz, 1H); 7.35 (d, J=8.8 Hz, 1H); 7.53 (d, J=2.4 Hz, 1H); 7.6 (s, 1H).

MS (m/z): 285 (100); 270; 249; 180.

EXAMPLE 18

3,8-dimethyl-5,6-dihydroimidazo[5,1-a]-β-carboline methane sulfonate

The procedure of Example 1 was followed using 5-methyltryptamine and N-acetylglycine as substrate during operating mode A. The amide obtained was used directly in the cyclization reaction of operating mode C.

$^1$H NMR (300 MHz, $CDCl_3$:$CD_3OD$/90:10): 2.43 (s, 3H); 2.61 (s, 3H); 2.85 (s, 3H); 3.14 (t, J=7 Hz, 2H); 4.08 (t, J=7 Hz, 2H); 7.05 (d, 8.6 Hz, 1H); 7.28 (s, 1H); 7.32 (d, J=8.6 Hz, 1H); 7.51 (s, 1H)

MS (m/z) 237 (50); 129; 73; 55 (100).

EXAMPLE 19

3,8,11-trimethyl-5,6-dihydroimidazo[5,1-a]-β-carboline methane sulfonate

The procedure of Example 1 was followed using 5-methyltryptamine and N-acetylglycine as substrate during operating mode A.

$^1$H NMR ($CDCl_3$:$CD_3OD$/90:10): 2.40 (s, 3H); 2.70 (s, 3H); 2.75 (s, 3H); 3.2 (t, J=6.9 Hz, 2H); 3.75 (s, 3H); 4.18 (t, J=6.9 Hz, 2H); 7.07 (d, J=8.5 Hz, 1H), 7.21 (d, J=8.5 Hz, 1H); 7.27 (s, 1H); 7.50 (s, 1H).

MS (m/z) 251 (100); 235; 203.

EXAMPLE 20

11-ethyl-3,8-dimethyl-5,6-dihydroimidazo-[5,1-a]-β-carboline methane sulfonate

The procedure of Example 1 was followed using 5-methyltryptamine and N-acetylglycine as substrate during operating mode A. The alkylation agent for operating mode B was ethyl bromide.

$^1$H NMR (300 MHz, $CDCl_3$:$CD_3OD$/90:10): 1.32 (t, J=7.2 Hz, 3H); 2.40 (s, 3H); 2.72 (s, 3H); 2.78 (s, 3H); 3.21 (t, J=6.9 Hz, 2H); 4.19 (m, 4H); 7.08 (d, J=8.4 Hz, 1H); 7.20 (d, J=8.4 Hz, 1H); 7.29 (s, 1H); 7.45 (s, 1H).

MS (m/z): 265 (100); 250; 236; 223.

EXAMPLE 21

8-fluoro-3-methyl-5,6-dihydroimidazo[5,1-a]-β-carboline methane sulfonate

The procedure of Example 1 was followed using 5-fluorotryptamine and N-acetylglycine as substrate during operating mode A. The amide obtained was used directly in the cyclization reaction of operating mode C.

$^1$H NMR (300 MHZ, $CDCl_3$:$CD_3OD$/90:10): 2.60 (s, 3H); 2.75 (s, 3H); 3.09 (t, J=7 Hz, 2H); 4.10 (t, J=7 Hz, 2H); 6.87 (dt, J=2.4 and 9 Hz, 1H), 7.02 (dd, J=2.4 and 9 Hz, 1H); 7.26 (dd, J=3 and 9 Hz, 1H); 7.50 (s, 1H).

MS (m/z) 241 (100); 226; 199; 172.

EXAMPLE 22

8-bromo-3-methyl-5,6-dihydroimidazo[5,1-a]-β-carboline methane sulfonate

The procedure of Example 1 was followed using 5-bromotryptamine and N-acetylglycine as substrate during operating mode A. The amide obtained was used directly in the cyclization reaction of operating mode C.

$^1$H NMR (300 MHz, $CDCl_3$:$CD_3OD$/90:10): 2.68 (s, 3H); 2.86 (s, 3H); 3.19 (t, J=7.2 Hz, 2H); 4.20 (t, J=7.2 Hz, 2H); 7.28 (m, 2H); 7.34 (s, 1H); 7.58 (s, 1H); 7.61 (s, 1H).

MS (m/z) 301/302 (100); 286; 259; 234.

EXAMPLE 23

8-fluoro-3,11-dimethyl-5,6-dihydroimidazo-[5,1-a]-β-carboline methane sulfonate

The procedure of Example 1 was followed using 5-fluorotryptamine and N-acetylglycine as substrate during operating mode A.

$^1$H NMR (300 MHz, CDCl$_3$:CD$_3$OD/90:10): 2.78 (s, 3H); 2.83 (s, 3H); 3.25 (t, J=6.9 Hz, 2H); 4.31 (t, J=6.9 Hz, 2H); 7.07 (dt, J=2.4 and 9 Hz, 1H); 7.22 (dd, J=2.4 and 9 Hz, 1H); 7.32 (dd, J=3 and 9 Hz, 1H); 7.66 (s, 1H).

MS (m/z) 255 (100); 213; 185; 128.

EXAMPLE 24

8-fluoro-11-ethyl-3-methyl-5,6-dihydro-imidazo[5,1-a]-β-carboline methane sulfonate The procedure of Example 1 was followed using 5-fluorotryptamine and N-acetylglycine as substrate during operating mode A. The alkylation agent for operating mode B was ethyl bromide.

$^1$H NMR (CDCl$_3$:CD$_3$OD/90:10): 1.32 (t, J=7.2 Hz, 3H); 2.70 (s, 3H); 2.80 (s, 3H); 3.16 (t, J=6.9 Hz, 2H); 4.2 (m, 4H); 6.97 (dt, J=2.4 and 9 Hz, 1H), 7.13 (dd, J=2.4 and 9 Hz, 1H); 7.23 (dd, J=4 and 9 Hz, 1H); 7.65 (s, 1H).

MS (m/z): 269 (100); 254; 227; 199.

EXAMPLE 25

8-bromo-11-ethyl-3-methyl-5,6-dihydro-imidazo[5,1-a]-β-carboline methane sulfonate The procedure of Example 1 was followed using 5-bromotryptamine and N-acetylglycine as substrate during operating mode A. The alkylation agent for operating mode B was ethyl bromide.

$^1$H NMR (300 MHz, CDCl$_3$:CD$_3$OD/90:10): 1.32 (t, J=7 Hz, 3H); 2.70 (s, 3H); 2.75 (s, 3H); 3.18 (t, J=7 Hz, 2H); 3.59 (s, 3H); 4.20 (m, 4H); 7.19 (d, J=8.7 Hz, 1H); 7.30 (dd, J=1.8 and 8.7 Hz, 1H); 7.53 (s, 1H); 7.63 (d, J=1.8 Hz, 1H).

MS (m/z): 329/330 (100); 316; 300; 273.

The dihydroimidazo[5,1-a]-β-carboline derivatives of the invention, in particular those in the form of the methyl sulfonate, (soluble), were tested in chicks, and certain compounds that were active in the chick were administered in single doses to six Beagle dogs of both sexes for a polysomnographic study of at least 4 hours duration.

Experimental Protocol for the Chick

JA 657 chicks from Couvoir Gauguet, 44 Le Pin, were accustomed for at least 6 days to an alternating program of light and darkness with 12 hours of daylight and 12 hours of darkness at a regulated temperature of 25±2° C. They were fed ad libitum and were placed under test compounds in a vivarium in groups of 3 individuals with a mean weight of 100±10 g on the day of the test. At that age in this species, there is no effective meningeal (hemato-encephalic) barrier. The test products were injected in 3 doses (1, 3 and 10 mg/kg) intramuscularly (IM) in solution or in an aqueous suspension (1 drop of Tween 80 per ml), each to two batches of 3 chicks which were observed over 90 minutes. For each test series (18 vivaria), there was at least one batch of negative control chicks receiving the same volume (0.2 ml IM) of water for injectable preparations.

During the 90 minute observation period, the chicks were strongly stimulated every 15 minutes by presenting a full feeding trough, and each 5 minute period was given a grade from among the following 5 states, corresponding to the state of alertness over that period:

Mobile, sitting alert, drowsy, asleep, sleep-like state. The parameters studied were the time to torpor (TA) passed between injection and the first stage of sleep, the duration of the first sleep (TS) and the total sedation time over the period (Tsed), expressed in minutes and as a % of the period (Sed).

To compare the results of tests carried out at different dates, the extension of the duration of the first sleep TS compared with the test controls was recorded.

Results

In the untested chick of the same age, the wake-sleep cycle lasts 20 to 30 minutes during the day. Thus, it appears that from a dose of 1 mg, at least 11 compounds (out of 20) induced a very substantial reduction in locomotive activity, as shown by a first sleep period TS of more than 20 minutes.

At higher doses, the number of test products in this category changed to 18/20 and 20/20 for 3 and 10 mg/kg.

There is a clear positive dose-effect relationship for the majority of the test compounds, with a reduction in the onset of torpor when the dose is increased.

Over 90 minutes, the difference in the sedation time compared with that observed using a placebo was more than 52 minutes for 2 compounds from a dose of 1 mg/kg, for 4 compounds at 3 mg/kg and for 12 compounds at 10 mg/kg.

TABLE II (Dose: 1 mg/kg)

| COMPOUNDS | TA Mins | TS Mins | Tsed Mins | Sed % | TS (mins) Placebo diff'ce |
|---|---|---|---|---|---|
| Example 1 | 7 | 56.5 | 64.5 | 71.7 | 56 |
| Example 2* | 16 | 3 | 25 | 27.8 | 3 |
| Example 3* | 10 | 40 | 66.51 | 73.9 | 36 |
| Example 4* | 16.5 | 38 | 53.01 | 58.9 | 34 |
| Example 5* | 20.5 | 33 | 52.47 | 58.3 | 29 |
| Example 6* | 11 | 56.5 | 65.97 | 73.3 | 52.5 |
| Example 7* | 16.5 | 16 | 46 | 41.4 | 16 |
| Example 8 | 16 | 21.5 | 38 | 42.2 | 21 |
| Example 9 | 22 | 3 | 24.5 | 27.2 | 2.8 |
| Example 10 | 15 | 5 | 38 | 42.2 | 4.7 |
| Example 11 | 40 | 0 | 26.5 | 29.4 | −0.3 |
| Example 12 | 10 | 39.5 | 46.5 | 51.7 | 39 |
| Example 13 | 16.5 | 33.5 | 52 | 57.8 | 33 |
| Example 14* | 7 | 35.5 | 62.865 | 63.5 | 32 |
| Example 15 | 12.5 | 12 | 21.5 | 23.9 | 21 |
| Example 16 | 11.5 | 15 | 37 | 41 | 14.7 |
| Example 17 | 12 | 12 | 37 | 41.1 | 11.7 |
| Example 18 | 5 | 32.5 | 62.5 | 69.4 | 24 |
| Example 19 | 4 | 17.5 | 44.5 | 49.4 | 11 |
| Example 20 | 2 | 65.5 | 72 | 80 | 57 |

*in the form of the free base

TABLE III (Dose: 3 mg/kg)

| COMPOUNDS | TA Mins | TS Mins | Tsed Mins | Sed % | TS (mins) Placebo diff'ce |
|---|---|---|---|---|---|
| Example 1 | 4.5 | 78.5 | 78.5 | 87.2 | 78 |
| Example 2* | 8.5 | 41 | 62.5 | 69.4 | 41 |
| Example 3* | 7 | 66.5 | 71.0 | 78.9 | 62.5 |
| Example 4* | 14 | 22.5 | 65.5 | 72.8 | 18.5 |
| Example 5* | 14.5 | 53 | 69.0 | 76.7 | 49 |
| Example 6* | 12.5 | 72.5 | 72.5 | 80.6 | 68.5 |
| Example 7* | 16.5 | 27 | 45.5 | 41 | 27 |
| Example 8 | 8.5 | 33 | 54 | 60 | 32.7 |
| Example 9 | 17.5 | 13.5 | 26.5 | 29.4 | 13 |
| Example 10 | 30 | 1 | 11 | 12.2 | 0.7 |
| Example 11 | 15 | 7 | 34.5 | 38.3 | 6.7 |
| Example 12 | 3.5 | 42 | 57.5 | 63.9 | 41.7 |
| Example 13 | 9.5 | 73 | 73 | 81.1 | 73 |
| Example 14* | 15 | 34 | 61.2 | 68 | 31.5 |
| Example 15 | 7 | 29.5 | 40.5 | 45 | 29 |

TABLE III-continued (Dose: 3 mg/kg)

| COMPOUNDS | TA Mins | TS Mins | Tsed Mins | Sed % | TS (mins) Placebo diff'ce |
|---|---|---|---|---|---|
| Example 16 | 13.5 | 20.5 | 30.5 | 33.9 | 20 |
| Example 17 | 7.5 | 23.5 | 30 | 33.3 | 23 |
| Example 18 | 4.5 | 30.5 | 57.5 | 63.9 | 22.5 |
| Example 19 | 3.5 | 46.5 | 56.5 | 62.8 | 38.5 |
| Example 20 | 1.5 | 51.5 | 71.5 | 79.4 | 43.5 |

*in the form of the free base

TABLE IV (Dose: 10 mg/kg)

| COMPOUNDS | TA Mins | TS Mins | Tsed Mins | Sed % | TS (mins) Placebo diff'ce |
|---|---|---|---|---|---|
| Example 1 | 1 | 86 | 87 | 96.7 | 85.7 |
| Example 2* | 7 | 83 | 83 | 92.2 | 83 |
| Example 3* | 6.5 | 77.5 | 78.0 | 86.7 | 73.5 |
| Example 4* | 8.5 | 81.5 | 81.5 | 90.6 | 76.5 |
| Example 5* | 13.5 | 40.5 | 56.5 | 62.8 | 36.5 |
| Example 6* | 12.5 | 72.5 | 74.0 | 82.2 | 68.5 |
| Example 7* | 12.5 | 38.5 | 53.5 | 48.2 | 38.5 |
| Example 8 | 5.5 | 41 | 68.5 | 76.1 | 40.7 |
| Example 9 | 16.5 | 15.5 | 38.5 | 42.8 | 15 |
| Example 10 | 11.5 | 12.5 | 27 | 30 | 12 |
| Example 11 | 6 | 9.5 | 18.5 | 20.6 | 9 |
| Example 12 | 1 | 89 | 89 | 98.9 | 88.7 |
| Example 13 | 4 | 86 | 86 | 95.6 | 85.7 |
| Example 14* | 7 | 28 | 63 | 70 | 25.5 |
| Example 15 | 1 | 70 | 72 | 80 | 69.7 |
| Example 16 | 7.5 | 31 | 52.5 | 58.3 | 52 |
| Example 17 | 5 | 43.5 | 60.5 | 67.2 | 43 |
| Example 18 | 7.5 | 76 | 81.5 | 90.6 | 68 |
| Example 19 | 3.5 | 60 | 67.5 | 75.0 | 52 |
| Example 20 | 1.5 | 87.5 | 87.5 | 97.2 | 81.5 |

*in the form of the free base

Experimental Protocol for the Dog

Polysomnographic tests were carried out for each of the three products from the series, on 6 dogs of both sexes, adults from the certified breeding kennels at HARLAN, 03 Gannat, using stainless steel electrodes surgically implanted for the duration of the test in contact with the frontal bones through the sinus, facing the motor regions of the encephalus. The Nishino et al method adapted by Tafani, Valin et al has been described elsewhere. It comprised recording two traces for eye movements, one trace for muscular movements (concentric electrode in the nape muscles) and two electroencephalographic (EEG) traces. The digital EEG trace was recorded using a Nicollet Schwarzer polygraph or the like (DELTAMED Coherence 2 and 3, MEI Galileo NT) for 4 hours after administering a 00 gelule containing 0, 16 or 48 mg of the test product (i.e. a mean of 0,1 and 3 mg/kg of live weight).

Each dog was monitored for 4 hours twice a day over two days, morning and afternoon, after one week's acclimatization to the monitoring cage, a 1 m² , 80 cm high stainless steel cage of the SHOR-LINE type. For each dog, monitoring always commenced at the same time. A meal was distributed 30 minutes before starting monitoring.

The polysomnographic traces could differentiate between at least 4 stages for each consecutive 30 second period: awake, somnolence, slow sleep and paradoxal sleep. The latency of the appearance of each of the first nonalert episodes and the duration of each of the stages per 2 hour period were recorded for each dog. Comparing the means allowed the effect of the test products on the sleep microstructure to be studied.

Results:

Latencies: Tables V to VII:

TABLE V

| Dose | Somnolence minutes | Slow wave sleep (SWS) minutes | Paradoxal (REM) sleep minutes |
|---|---|---|---|
| Placebo 1 + 2 | 70 ± 6 | 98 ± 20 | 137 ± 4 |
| Example 2 (1 mg) | 40 ± 14.7 | 44 ± 16.3 | 114 ± 53 |
| Example 2 (3 mg) | 37 ± 6.7 | 45 ± 5.4 | 63 ± 21.1 |

TABLE VI

| Dose | Somnolence minutes | Slow wave sleep (SWS) minutes | Paradoxal (REM) sleep minutes |
|---|---|---|---|
| Placebo 1 | 69 ± 58 | 79 ± 60 | 100 ± 62 |
| Example 13 (1 mg) | 25 ± 11.6 | 32 ± 11.5 | 63 ± 28.2 |
| Placebo 2 | 40 ± 13.1 | 50 ± 23.8 | 62 ± 22.4 |
| Example 13 (3 mg) | 27 ± 9.1 | 35 ± 11 | 56 ± 19.5 |

TABLE VII

| Dose | Somnolence minutes | Slow wave sleep (SWS) minutes | Paradoxal (REM) sleep minutes |
|---|---|---|---|
| Placebo 1 | 71 ± 39.8 | 102 ± 71.8 | 125 ± 66.9 |
| Example 1 (1 mg) | 47 ± 19.1 | 52 ± 24.8 | 101 ± 80.3 |
| Placebo 2 | 44 ± 20.4 | 61 ± 27.6 | 87 ± 30.2 |
| Example 1 (3 mg) | 21 ± 7.1 | 27 ± 8.0 | 50 ± 22.2 |

The three test products show a clear reduction in the latency of the first somnolence, which is clearer in the 3 mg/kg dose for the product of Example 1. The latency of the first slow sleep episode (characterized by spikes on the EEG traces) was halved compared with the overall test products.

The three compounds induce a positive hypnagogic effect.

Time passed at each alert stage: Tables VIII to X.

TABLE VIII

| Dose | Alertness minutes | Somnolence minutes | SWS minutes | REM minutes |
|---|---|---|---|---|
| Placebo 1 + 2 | 147 ± 35.5 | 25 ± 10.3 | 59 ± 21.9 | 8.5 ± 5.4 |
| Example 2 (1 mg) | 136 ± 40.3 | 31 ± 4.6 | 59 ± 20.5 | 13.5 ± 10.6 |
| Example 2 (3 mg) | 123 ± 30.5 | 36 ± 15.4 | 60 ± 26.9 | 20 ± 9.5 |

TABLE IX

| Dose | Alertness minutes | Somnolence minutes | SWS minutes | REM minutes |
|---|---|---|---|---|
| Placebo 1 | 156 ± 38.5 | 26 ± 11.3 | 39 ± 23.9 | 19 ± 11.4 |
| Example 13 (1 mg) | 135 ± 44.3 | 24 ± 2.6 | 57 ± 26.5 | 21 ± 13.6 |

TABLE IX-continued

| Dose | Alertness minutes | Somnolence minutes | SWS minutes | REM minutes |
|---|---|---|---|---|
| Placebo 2 | 140 ± 27.9 | 32 ± 7.3 | 47 ± 19.9 | 21 ± 10 |
| Example 13 (3 mg) | 122 ± 36.5 | 31 ± 7 | 61 ± 24.9 | 26 ± 13.5 |

TABLE X

| Dose | Alertness minutes | Somnolence minutes | SWS minutes | REM minutes |
|---|---|---|---|---|
| Placebo 1 | 154 ± 35.2 | 30 ± 16.0 | 45 ± 19.4 | 11 ± 8.5 |
| Example 1 (1 mg) | 139 ± 69.1 | 27 ± 10.4 | 51 ± 42.3 | 23 ± 19.1 |
| Placebo 2 | 134 ± 36.5 | 35 ± 21.4 | 50 ± 34.8 | 20 ± 10.8 |
| Example 1 (3 mg) | 106 ± 34.7 | 40 ± 10.9 | 65 ± 30.2 | 29 ± 13.7 |

Over the four hours of monitoring, a tendency for the alertness period to reduce was observed, in particular for the dose of 3 mg/kg for the three compounds. This reduction in alertness was accomplished essentially by an increase in the slow sleep and paradoxal sleep stages.

The observed effects were manifested more clearly during the first two hours, particularly for the dose of 1 mg/kg, which could correspond to the product elimination kinetics.

The three compounds exhibit hypnotic properties.

In contrast to known compounds, there was no modification in the percentage somnolence nor in that of the paradoxal sleep in the nonalert period.

The imidazopyridoindole derivatives of the invention all exhibited a pharmacological activity on the central nervous system of at least two animal species. They reduced alertness, accelerating the onset of sleep (positive hypnagogic effect). In the chick and the dog, there was a reduction in alert activity. In this latter species, there was no modification in sleep ultrastructure. Thus, they are useful as drugs, in particular as hypnotics.

The invention claimed is:

1. Compounds of dihydroimidazo[5,1-a]-β-carboline with general formula (I):

(I)

in which:

$R_1$, $R_2$, $R_3$ and $R_4$, which may be identical or different, independently represent a hydrogen atom, a halogen atom, a linear or branched ($C_1$-$C_6$) alkyl group, a hydroxyl group, a linear or branched ($C_1$-$C_6$) alkoxy group, a linear or branched trihalogeno ($C_1$-$C_6$) alkyl group, a linear or branched trihalogeno ($C_1$-$C_6$) alkoxy group, a nitro group, a cyano group, an amino group, a linear or branched ($C_1$-$C_6$) alkylamino group, a linear or branched di ($C_1$-$C_6$) alkylamino group, an aryl group, a linear or branched aryl ($C_1$-$C_6$) alkyl group, a carboxyl group, a linear or branched ($C_1$-$C_6$) alkylcarbonyloxy group, a linear or branched ($C_1$-$C_6$) acyl group, an aryloxy group or a linear or branched aryl ($C_1$-$C_6$) alkoxy group;

$R_5$ represents a hydrogen atom, a linear or branched ($C_1$-$C_6$) alkyl group or a linear or branched aryl ($C_1$-$C_6$) alkyl group; and $R_6$ and $R_7$, which may be identical or different, independently represent a hydrogen atom, a halogen atom, a linear or branched ($C_1$-$C_6$) alkyl group, a hydroxyl group, a linear or branched ($C_1$-$C_6$) alkoxy group, a linear or branched trihalogeno ($C_1$-$C_6$) alkyl group, a linear or branched trihalogeno ($C_1$-$C_6$) alkoxy group, a cyano group, an amino group, a linear or branched ($C_1$-$C_6$) alkylamino group, a linear or branched di ($C_1$-$C_6$) alkylamino group, an aryl group, a linear or branched aryl ($C_1$-$C_6$) alkyl group, a carboxyl group, a linear or branched ($C_1$-$C_6$) alkylcarbonyloxy group, a linear or branched ($C_1$-$C_6$) acyl group, an aryloxy group, or a linear or branched aryl ($C_1$-$C_6$) alkoxy group;

with the exception, however, of compounds with general formula I in which $R_1$ to $R_6$ represent a hydrogen atom and $R_7$ represents a $CH_3$ group or a phenyl group; their isomers and their addition salts with a pharmaceutically acceptable acid.

2. The compounds as claimed in claim 1, wherein:

$R_1$, $R_3$ and $R_4$ represent a hydrogen atom;

$R_6$ and $R_7$ independently represent hydrogen, a linear or branched ($C_1$-$C_6$) alkyl group or an aryl group, in particular a phenyl group; and $R_5$ represents a hydrogen atom, or a linear or branched ($C_1$-$C_6$) alkyl group.

3. The compounds as claimed in claim 1, wherein:

$R_2$ represents a hydrogen atom, a halogen atom [(fluorine, chlorine or bromine)], a linear or branched ($C_1$-$C_6$) alkyl group, a hydroxyl group or a linear or branched ($C_1$-$C_6$) alkoxy group.

4. The compounds as claimed in claim 1, which are selected from the following compounds:

3,11-dimethyl-5,6-dihydroimidazo[5,1-a]-β-carboline methane sulfonate;

8-methoxy-3-methyl-5,6-dihydroimidazo[5,1-a]-β-carboline methane sulfonate;

8-methoxy-5,6-dihydroimidazo[5,1-a]-β-carboline;

8-methoxy-3-methyl-1-phenyl-5,6-dihydroimidazo[5,1-a]-β-carboline;

1-ethyl-8-methoxy-3-methyl-5,6-dihydroimidazo[5,1-a]-β-carboline;

8-methoxy-3-isopropyl-5,6-dihydroimidazo[5,1-a]-β-carboline;

8-methoxy-3-propyl-5,6-dihydroimidazo[5,1-a]-β-carboline;

8-methoxy-11-methyl-3-propyl-5,6-dihydroimidazo[5,1-a]-β-carboline methane sulfonate;

8-methoxy-3,11-dimethyl-5,6-dihydroimidazo[5,1-a]-β-carboline methane sulfonate;

8-hydroxy-3,11-dimethyl-5,6-dihydroimidazo[5,1-a]-β-carboline methane sulfonate;

8-hydroxy-3-methyl-5,6-dihydroimidazo[5,1-a]-β-carboline methane sulfonate;

8-chloro-3-methyl-5,6-dihydroimidazo[5,1-a]-β-carboline methane sulfonate;

8-methoxy-3-phenyl-5,6-dihydroimidazo[5,1-a]-β-carboline;

11-ethyl-3-methyl-5,6-dihydroimidazo[5,1-a]-β-carboline methane sulfonate;

8-chloro-3,11-dimethyl-5,6-dihydroimidazo[5,1-a]-β-carboline methane sulfonate;
8-chloro-3-methyl-11-ethyl-5,6-dihydroimidazo[5,1-a]-β-carboline methane sulfonate;
3,8-dimethyl-5,6-dihydroimidazo[5,1-a]-β-carboline methane sulfonate;
3,8,11-trimethyl-5,6-dihydroimidazo[5,1-a]-β-carboline methane sulfonate;
11-ethyl-3,8-dimethyl-5,6-dihydroimidazo[5,1-a]-β-carboline methane sulfonate;
8-fluoro-3-methyl-5,6-dihydroimidazo[5,1-a]-β-carboline methane sulfonate;
8-bromo-3-methyl-5,6-dihydroimidazo[5,1-a]-β-carboline methane sulfonate;
8-fluoro-3,11-dimethyl-5,6-dihydroimidazo[5,1-a]-β-carboline methane sulfonate;
8-fluoro-11-ethyl-3-methyl-5,6-dihydroimidazo[5,1-a]-β-carboline methane sulfonate;
8-bromo-11-ethyl-3-methyl-5,6-dihydroimidazo[5,1-a]-β-carboline methane sulfonate.

5. A method for preparing compounds with formula (I) as claimed in claim 1, wherein a compound with formula (II):

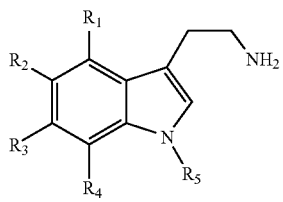

in which $R_1$, $R_2$, $R_3$, $R_4$ and $R_5$ have the meanings given in formula (I), is reacted under peptide coupling synthesis conditions with a compound with formula (III):

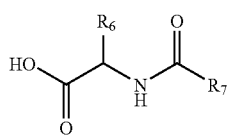

In which $R_6$ and $R_7$ are as defined in formula (I), to produce a compound with formula (IV):

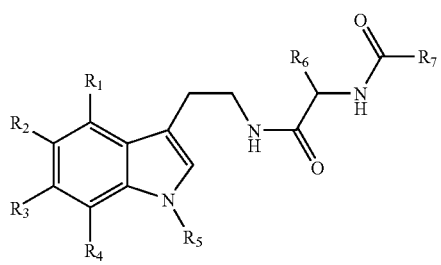

In which $R_1$, $R_2$, $R_3$, $R_4$, $R_5$, $R_6$ and $R_7$ have the meanings defined above, the compound with formula (IV) being treated in the presence of phosphorous oxychloride in a solvent to produce compounds with formula (I):

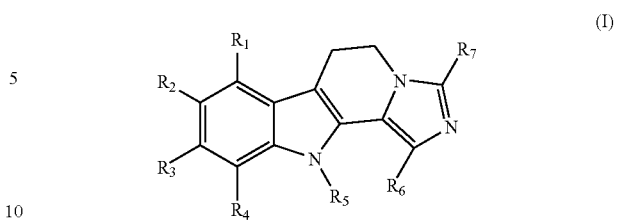

in which $R_1$, $R_2$, $R_3$, $R_4$, $R_5$, $R_6$ and $R_7$ are as defined above, the compounds with general formula (I) being transformed if appropriate into their addition salts with a pharmaceutically acceptable acid.

6. Pharmaceutical compositions comprising, as the active principle, at least one compound with formula (I) or one of its addition salts with a pharmaceutically acceptable acid as claimed in claim 1, in combination with one or more nontoxic and pharmaceutically acceptable excipients or inert vehicles.

7. The method according to claim 5, wherein the compound of formula (IV) is treated in the presence of phosphorus oxychloride in toluene.

8. A method for reducing alertness and/or for accelerating the onset of sleep in an animal in need of same, said method comprising administering an effective amount of a compound as claimed in claim 1 to said animal.

9. A method for reducing alertness and/or for accelerating the onset of sleep in an animal in need of same, said method comprising administering to said animal an effective amount of a compound selected from the group consisting of:
3,11-dimethyl-5,6-dihydroimidazo[5,1-a]-β-carboline methane sulfonate;
8-methoxy-3-methyl-5,6-dihydroimidazo[5,1-a]-β-carboline methane sulfonate;
8-methoxy-5,6-dihydroimidazo[5,1-a]-β-carboline;
8-methoxy-3-methyl-1-phenyl-5,6-dihydroimidazo[5,1-a]-β-carboline;
1-ethyl-8-methoxy-3-methyl-5,6-dihydroimidazo[5,1-a]-β-carboline;
8-methoxy-3-isopropyl-5,6-dihydroimidazo[5,1-a]-β-carboline;
8-methoxy-3-propyl-5,6-dihydroimidazo[5,1-a]-β-carboline;
8-methoxy-11-methyl-3-propyl-5,6-dihydroimidazo[5,1-a]-β-carboline methane sulfonate;
8-methoxy-3,11-dimethyl-5,6-dihydroimidazo[5,1-a]-β-carboline methane sulfonate;
8-hydroxy-3,11-dimethyl-5,6-dihydroimidazo[5,1-a]-β-carboline methane sulfonate;
8-hydroxy-3-methyl-5,6-dihydroimidazo[5,1-a]-β-carboline methane sulfonate;
8-chloro-3-methyl-5,6-dihydroimidazo[5,1-a]-β-carboline methane sulfonate;
8-methoxy-3-phenyl-5,6-dihydroimidazo[5,1-a]-β-carboline;
11-ethyl-3-methyl-5,6-dihydroimidazo[5,1-a]-β-carboline methane sulfonate;
8-chloro-3,11-dimethyl-5,6-dihydroimidazo[5,1-a]-β-carboline methane sulfonate;
8-chloro-3-methyl-11-ethyl-5,6-dihydroimidazo[5,1-a]-β-carboline methane sulfonate;
3,8-dimethyl-5,6-dihydroimidazo[5,1-a]-β-carboline methane sulfonate;

3,8,11-trimethyl-5,6-dihydroimidazo[5,1-a]-β-carboline methane sulfonate;

11-ethyl-3,8-dimethyl-5,6-dihydroimidazo[5,1-a]-β-carboline methane sulfonate;

8-fluoro-3-methyl-5,6-dihydroimidazo[5,1-a]-β-carboline methane sulfonate;

8-bromo-3-methyl-5,6-dihydroimidazo[5,1-a]-β-carboline methane sulfonate;

8-fluoro-3,11-dimethyl-5,6-dihydroimidazo[5,1-a]-β-carboline methane sulfonate;

8-fluoro-11-ethyl-3-methyl-5,6-dihydroimidazo[5,1-a]-β-carboline methane sulfonate; and 8-bromo-11-ethyl-3-methyl-5,6-dihydroimidazo[5,1-a]-β-carboline methane sulfonate; and the corresponding free bases.

10. A pharmaceutical composition comprising, as the active principle, at least one compound of formula (I):

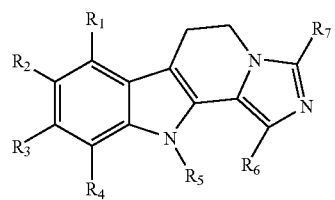

(I)

or an addition salt thereof with a pharmaceutically acceptable acid, in which:

$R_1$, $R_2$, $R_3$ and $R_4$, which may be identical or different, independently represent a hydrogen atom, a halogen atom, a linear or branched ($C_1$-$C_6$) alkyl group, a hydroxyl group, a linear or branched ($C_1$-$C_6$) alkoxy group, a linear or branched trihalogeno ($C_1$-$C_6$) alkyl group, a linear or branched trihalogeno ($C_1$-$C_6$) alkoxy group, a nitro group, a cyano group, an amino group, a linear or branched ($C_1$-$C_6$) alkylamino group, a linear or branched di ($C_1$-$C_6$) alkylamino group, an aryl group, a linear or branched aryl ($C_1$-$C_6$) alkyl group, a carboxyl group, a linear or branched ($C_1$-$C_6$) alkylcarbonyloxy group, a linear or branched ($C_1$-$C_6$) acyl group, an aryloxy group or a linear or branched aryl ($C_1$-$C_6$) alkoxy group;

$R_5$ represents a hydrogen atom, a linear or branched ($C_1$-$C_6$) alkyl group or a linear or branched aryl ($C_1$-$C_6$) alkyl group; and $R_6$ and $R_7$, which may be identical or different, independently represent a hydrogen atom, a halogen atom, a linear or branched ($C_1$-$C_6$) alkyl group, a hydroxyl group, a linear or branched ($C_1$-$C_6$) alkoxy group, a linear or branched trihalogeno ($C_1$-$C_6$) alkyl group, a linear or branched trihalogeno ($C_1$-$C_6$) alkoxy group, a cyano group, an amino group, a linear or branched ($C_1$-$C_6$) alkylamino group, a linear or branched di ($C_1$-$C_6$) alkylamino group, an aryl group, a linear or branched aryl ($C_1$-$C_6$) alkyl group, a carboxyl group, a linear or branched ($C_1$-$C_6$) alkylcarbonyloxy group, a linear or branched ($C_1$-$C_6$) acyl group, an aryloxy group, or a linear or branched aryl ($C_1$-$C_6$) alkoxy group;

in combination with one or more nontoxic and pharmaceutically acceptable excipients or inert vehicles.

11. A pharmaceutical composition, in unit dosage form, comprising a unit dosage amount of at least one compound of formula (I):

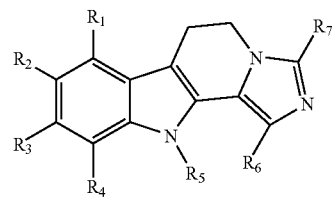

(I)

or an acid addition salt thereof with a pharmaceutically acceptable acid, in which:

$R_1$, $R_2$, $R_3$ and $R_4$, which may be identical or different, independently represent a hydrogen atom, a halogen atom, a linear or branched ($C_1$-$C_6$) alkyl group, a hydroxyl group, a linear or branched ($C_1$-$C_6$) alkoxy group, a linear or branched trihalogeno ($C_1$-$C_6$) alkyl group, a linear or branched trihalogeno ($C_1$-$C_6$) alkoxy group, a nitro group, a cyano group, an amino group, a linear or branched ($C_1$-$C_6$) alkylamino group, a linear or branched di ($C_1$-$C_6$) alkylamino group, an aryl group, a linear or branched aryl ($C_1$-$C_6$) alkyl group, a carboxyl group, a linear or branched ($C_1$-$C_6$) alkylcarbonyloxy group, a linear or branched ($C_1$-$C_6$) acyl group, an aryloxy group or a linear or branched aryl ($C_1$-$C_6$) alkoxy group;

$R_5$ represents a hydrogen atom, a linear or branched ($C_1$-$C_6$) alkyl group or a linear or branched aryl ($C_1$-$C_6$) alkyl group; and $R_6$ and $R_7$, which may be identical or different, independently represent a hydrogen atom, a halogen atom, a linear or branched ($C_1$-$C_6$) alkyl group, a hydroxyl group, a linear or branched ($C_1$-$C_6$) alkoxy group, a linear or branched trihalogeno ($C_1$-$C_6$) alkyl group, a linear or branched trihalogeno ($C_1$-$C_6$) alkoxy group, a cyano group, an amino group, a linear or branched ($C_1$-$C_6$) alkylamino group, a linear or branched di ($C_1$-$C_6$) alkylamino group, an aryl group, a linear or branched aryl ($C_1$-$C_6$) alkyl group, a carboxyl group, a linear or branched ($C_1$-$C_6$) alkylcarbonyloxy group, a linear or branched ($C_1$-$C_6$) acyl group, an aryloxy group, or a linear or branched aryl ($C_1$-$C_6$) alkoxy group;

said amount being effective to reduce alertness and/or accelerate the onset of sleep, in combination with one or more nontoxic and pharmaceutically acceptable excipients or inert vehicles.

12. A method for reducing alertness and/or for accelerating the onset of sleep in an animal in need of same, said method comprising administering an effective amount of a composition as claimed in claim 10 to said animal.

13. A method for reducing alertness and/or for accelerating the onset of sleep in an animal in need of same, said method comprising administering an effective amount of a composition as claimed in claim 11 to said animal.

14. A method for reducing alertness and/or for accelerating the onset of sleep in an animal in need of same, said method comprising administering to said animal an effective amount of a compound selected from the group consisting of:

3,11-dimethyl-5,6-dihydroimidazo[5,1-a]-β-carboline methane sulfonate;

8-methoxy-3-methyl-5,6-dihydroimidazo[5,1-a]-β-carboline methane sulfonate;

8-methoxy-5,6-dihydroimidazo[5,1-a]-β-carboline;

8-methoxy-3-methyl-1-phenyl-5,6-dihydroimidazo[5,1-a]-β-carboline;
1-ethyl-8-methoxy-3-methyl-5,6-dihydroimidazo[5,1-a]-β-carboline;
8-methoxy-3-isopropyl-5,6-dihydroimidazo[5,1-a]-β-carboline;
8-methoxy-3-propyl-5,6-dihydroimidazo[5,1-a]-β-carboline;
8-methoxy-11-methyl-3-propyl-5,6-dihydroimidazo[5,1-a]-β-carboline methane; sulfonate;
8-methoxy-3,11-dimethyl-5,6-dihydroimidazo[5,1-a]-β-carboline methane sulfonate;
8-hydroxy-3,11-dimethyl-5,6-dihydroimidazo[5,1-a]-β-carboline methane sulfonate;
8-hydroxy-3-methyl-5,6-dihydroimidazo[5,1-a]-β-carboline methane sulfonate;
3-methyl-5,6-dihydroimidazo[5,1-a]-β-carboline methane sulfonate;
8-chloro-3-methyl-5,6-dihydroimidazo[5,1-a]-β-carboline methane sulfonate;
8-methoxy-3-phenyl-5,6-dihydroimidazo[5,1-a]-β-carboline;
11-ethyl-3-methyl-5,6-dihydroimidazo[5,1-a]-β-carboline methane sulfonate;
8-chloro-3,11-dimethyl-5,6-dihydroimidazo[5,1-a]-β-carboline methane sulfonate;
8-chloro-3-methyl-11-ethyl-5,6-dihydroimidazo[5,1-a]-β-carboline methane sulfonate;
3,8-dimethyl-5,6-dihydroimidazo[5,1-a]-β-carboline methane sulfonate;
3,8,11-trimethyl-5,6-dihydroimidazo[5,1-a]-β-carboline methane sulfonate;
11-ethyl-3,8-dimethyl-5,6-dihydroimidazo[5,1-a]-β-carboline methane sulfonate;
8-fluoro-3-methyl-5,6-dihydroimidazo[5,1-a]-β-carboline methane sulfonate;
8-bromo-3-methyl-5,6-dihydroimidazo[5,1-a]-β-carboline methane sulfonate;
8-fluoro-3,11-dimethyl-5,6-dihydroimidazo[5,1-a]-β-carboline methane sulfonate;
8-fluoro-11-ethyl-3-methyl-5,6-dihydroimidazo[5,1-a]-β-carboline methane sulfonate; and
8-bromo-11-ethyl-3-methyl-5,6-dihydroimidazo[5,1-a]-β-carboline methane sulfonate; and the corresponding free bases.

* * * * *